(12) United States Patent
Kluczynski et al.

(10) Patent No.: US 7,251,034 B2
(45) Date of Patent: Jul. 31, 2007

(54) WAVELENGTH MODULATION SPECTROSCOPY METHOD

(75) Inventors: Pawel Kluczynski, Västra Frölunda (SE); Jack Margolis, Pasadena, CA (US); Jan Nygren, Göteborg (SE)

(73) Assignee: Siemens Aktiengesellschaft, Munich (DE)

( * ) Notice: Subject to any disclaimer, the term of this patent is extended or adjusted under 35 U.S.C. 154(b) by 213 days.

(21) Appl. No.: 11/011,691

(22) Filed: Dec. 14, 2004

(65) Prior Publication Data

US 2005/0140979 A1    Jun. 30, 2005

(30) Foreign Application Priority Data

Dec. 17, 2003    (EP)    .................................... 03029102

(51) Int. Cl.
*G01N 21/00*    (2006.01)

(52) U.S. Cl. ..................................................... 356/437

(58) Field of Classification Search ..................... None
See application file for complete search history.

(56) References Cited

U.S. PATENT DOCUMENTS

| | | | | |
|---|---|---|---|---|
| 5,572,031 | A * | 11/1996 | Cooper et al. | 250/343 |
| 6,351,309 | B1 * | 2/2002 | Bomse et al. | 356/437 |
| 6,356,350 | B1 * | 3/2002 | Silver et al. | 356/437 |
| 6,611,335 | B1 * | 8/2003 | Hovde | 356/437 |
| 7,116,422 | B2 * | 10/2006 | Larking et al. | 356/437 |
| 2005/0140979 | A1 * | 6/2005 | Kluczynski et al. | 356/425 |

OTHER PUBLICATIONS

Pawel Kluczynski and Ove Axner, "Theoretical description based on Fourier analysis of wavelength-modulation spectrometry in terms of analytical and background signals", Applied Optics, Optical Society of America, Washington, US, vol. 38, No. 27, Sep. 20, 1999, pp. 5803-5815, XP001176660.

Joel A. Silver, "Frequency-modulation spectroscopy for trace species detection: theory and comparison among experimental methods", Applied Optics, Optical Society of America, Washington, US, vol. 31, No. 6, Feb. 20, 1992, pp. 707-717, XP000248585.

* cited by examiner

*Primary Examiner*—Gregory J. Toatley, Jr.
*Assistant Examiner*—Jonathan Skovholt

(57) ABSTRACT

A wavelength modulation spectroscopy method for measuring the concentration of a gas component is provided. A gas sample portion of the light is passed through a reference gas comprising the gas component in a constant concentration. Afterwards, the light is detected by a reference detector. Another portion of the light is passed through the gas sample and thereafter to a measuring detector. The light emitted by the light source is modulated with a frequency, while the wavelength is swept over a molecular absorption line of the gas component. Demodulation of the detector outputs is made at a higher harmonic. In order to compensate for variations of the modulation parameters of the light source in real time, a mathematical description of the demodulated reference detector output based on Fourier analysis of the modulated light and on a mathematical expression for the absorption line is provided.

17 Claims, 2 Drawing Sheets

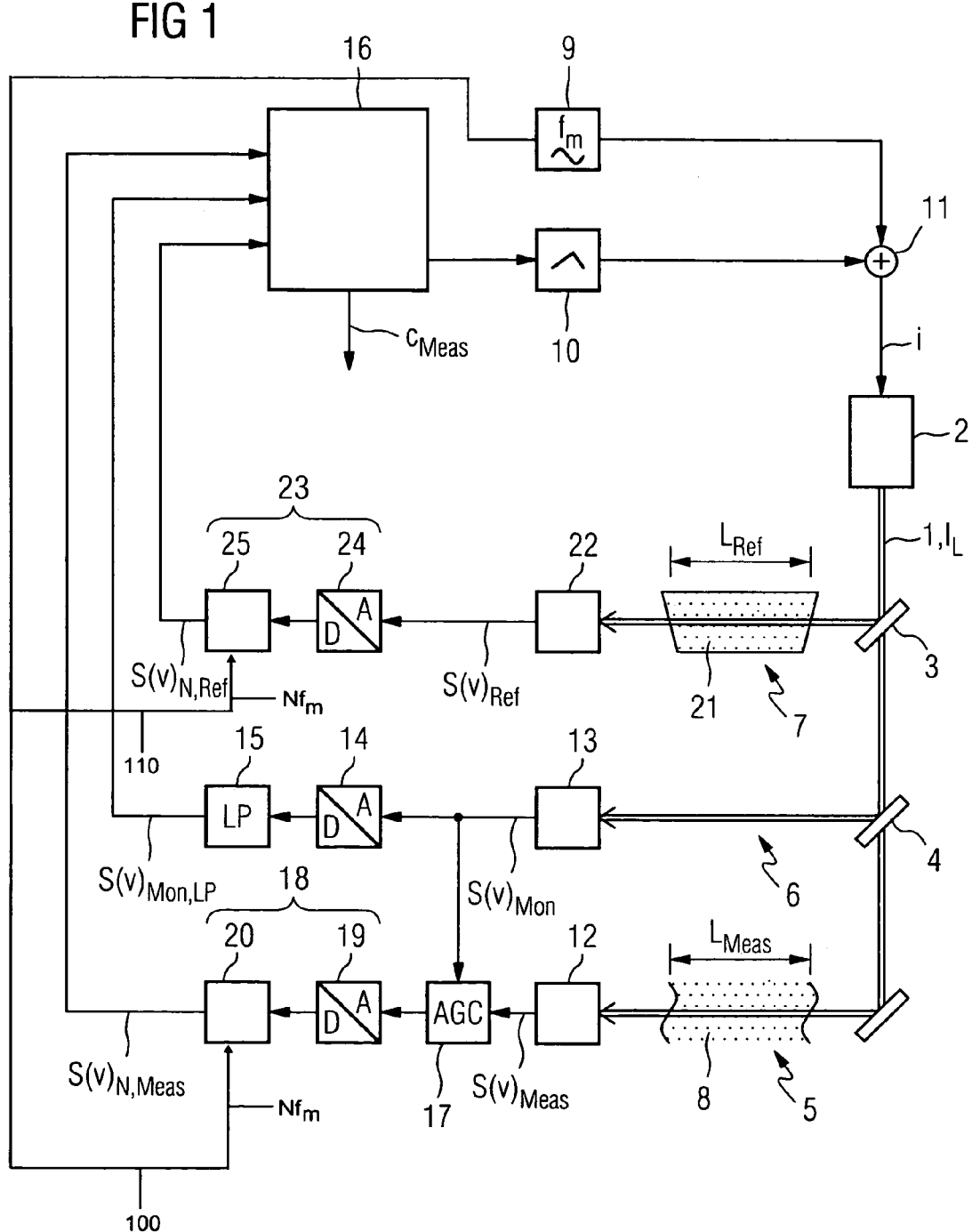

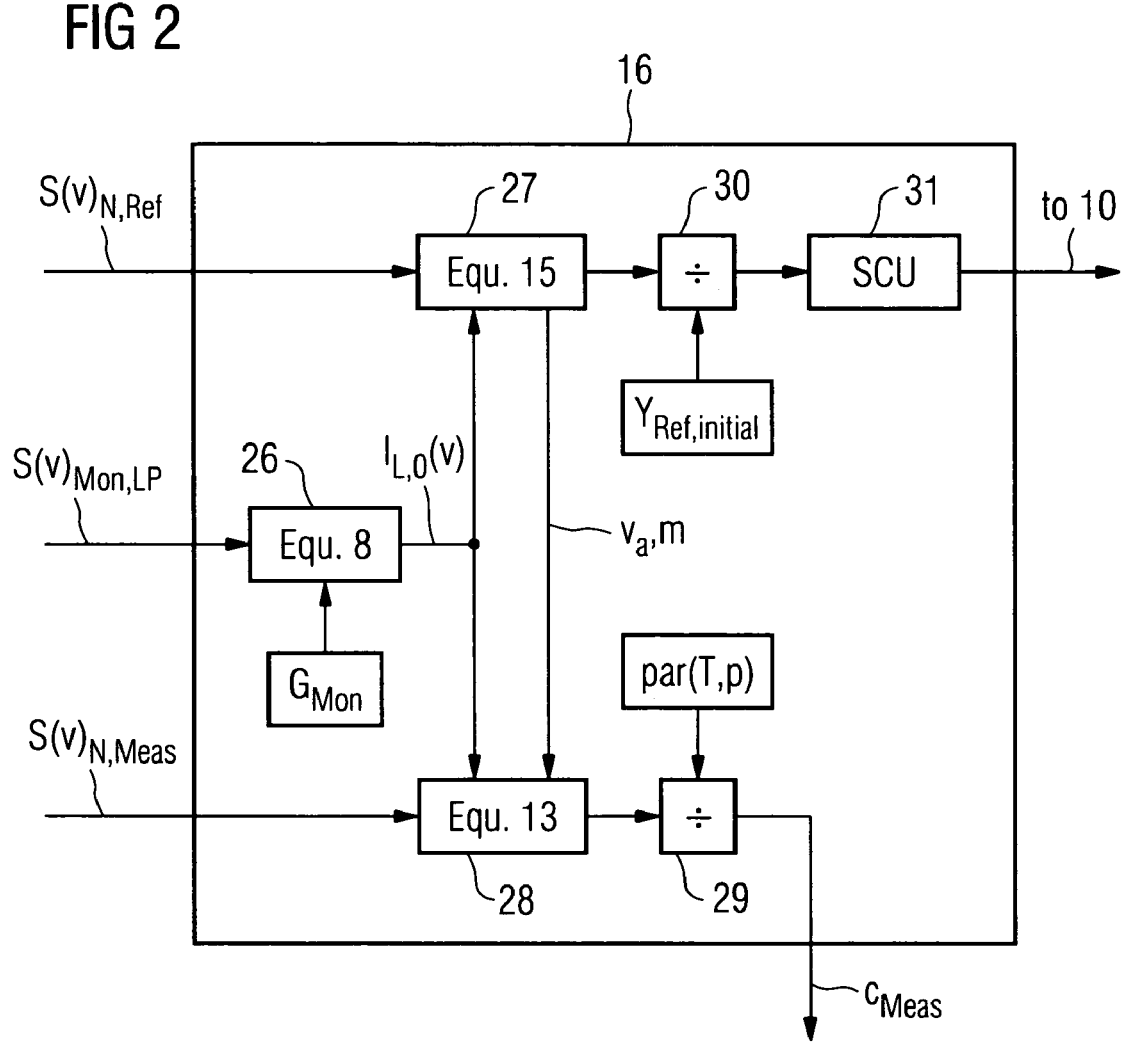

WAVELENGTH MODULATION SPECTROSCOPY METHOD

CROSS REFERENCE TO RELATED APPLICATIONS

This application claims priority to the European application No. 03029102.5, filed Dec. 17, 2003 and which is incorporated by reference herein in its entirety.

FIELD OF THE INVENTION

The invention relates to a wavelength modulation spectroscopy method for measuring the concentration of a gas component of interest in a gas sample.

BACKGROUND OF THE INVENTION

In wavelength modulation spectroscopy (WMS) for measuring the concentration of a gas component in a gas sample a portion of the light of a tunable light source, usually a continuously tunable laser such as a diode laser, is passed through a reference gas comprising the known gas component or another suitable gas component of constant concentration. Afterwards the light is detected by a reference detector. Another portion of the light is directed to a monitor detector for normalization purposes. Yet another portion of the light is passed through the gas sample and thereafter to a measuring detector. The light emitted by the light source is modulated with a frequency $f_m$, while the wavelength is swept over a molecular absorption line of the gas component. As the light propagates through the reference gas or gas sample, respectively, wavelength dependent absorption converts some of the wavelength modulation into an intensity modulation of the light. Thus, the light will have an overtone spectrum generated by the absorption process, the harmonic content of the spectrum being dependent on the width and shape of the molecular absorption line in the gas and the etalons in the spectroscopy system. When the light then impinges onto the reference detector or measuring detector, respectively, the detector outputs contain AC components at the modulation frequency $f_m$ and its higher harmonics $Nf_m$ (N=2, 3, 4, etc.). Demodulating the respective detector outputs at one of said higher harmonics $Nf_m$ shifts the measurement from frequencies near DC, where the light source is noisy, into a higher frequency range, where the noise is lower, thus improving the measurement sensitivity.

The modulation of the emitted light can most conveniently be accomplished by modulation of the injection current of the diode laser, which imposes modulation on the wavelength and to some extend on the intensity of the emitted light. As the demodulated $Nf_m$ absorption signal depends not only on the concentration of the measured gas but also on the modulation parameters of the light source, variations of these modulation parameters can affect the accuracy of the measurement.

SUMMARY OF THE INVENTION

Therefore, the invention seeks to provide a wavelength modulation spectroscopy method, which automatically compensates for variations of the modulation parameters of the light source in real time.

According to the invention this is achieved by the claims.

Preferred embodiments of the method and the system according to the invention are specified in the dependent claims.

The approach in this invention is to provide a mathematical description of the demodulated reference detector output based on Fourier analysis of the modulated light and on a mathematical expression for the absorption line, said mathematical description comprising the unknown modulation parameters of the light source, and determining said modulation parameters from the demodulated reference detector output and its mathematical description.

In a further step the concentration of the gas component in the gas sample can be determined by providing a further equivalent mathematical description of the demodulated measuring detector output based on Fourier analysis of the modulated light and on a mathematical expression for the absorption line, said further mathematical description comprising said modulation parameters and the unknown concentration of the gas component of interest in the gas sample, and determining said concentration of the gas component from the demodulated measuring detector output, its mathematical description and the determined modulation parameters.

BRIEF DESCRIPTION OF THE DRAWINGS

The invention will be now described by way of a preferred example and with reference to the accompanying drawing, wherein FIG. 1 shows a block diagram of a spectroscopy system in accordance with the invention, and FIG. 2 is a schematic block diagram of the calculating means of the system of FIG. 1.

DETAILED DESCRIPTION OF THE INVENTION

For a better understanding of the following description, reference is made to Applied Optics, 38 (1999) 5803-5815, where a theoretical description of the wavelength-modulation (WM) spectrometry technique is given. In the following description the optical frequency $\upsilon$ is used instead of the wavelength $\lambda$, which are inversely proportional to each other.

As FIG. 1 shows, the light 1 of a tunable light source 2, here a diode laser, is split by means of beam splitters 3 and 4 into a measurement path 5, a monitor path 6 and a reference path 7. Passing through the measurement path 5 the light 1 interacts with a sample 8, here a weakly absorbing gas sample, and is attenuated exponentially according to the Beer-Lambert law:

$$I = T_{Meas} I_L \cdot \exp[-\alpha(T, p, v, \gamma_{Meas}) L_{Meas}] \qquad \text{(Equation 1)}$$

$$= T_{Meas} I_L \cdot \exp\left[-A_{Meas}(T) c_{Meas} p_{Meas} \frac{1}{\pi \gamma_{Meas}} \chi(v, \gamma_{Meas}) L_{Meas}\right],$$

where I is the intensity of the light 1 after passing through the measurement path 5, $I_L$ is the intensity of the light 1 emitted from the light source 2, $T_{Meas}$ is a transmission factor over the measurement path 5, which transmission factor stands for the wavelength independent transmission of the optical system, $L_{Meas}$ is the length of the measurement path 5, $\alpha$ is the wavelength dependent absorption coefficient of the gas sample 8, A and $\chi$ represent the intensity and the peak-normalized shape of a molecular absorption line of a gas component of interest in the gas sample 8, respectively, $c_{Meas}$ is the concentration (mole fraction) of the absorbing gas component, $p_{Meas}$ is the total pressure in the measurement path 5 and $\gamma_{Meas}$ is the half width at half maximum (HWHM) of the absorption line. At atmospheric pressure the shape $\chi$ of the molecular absorption line is typically given by the Lorentzian line-shape function:

$$\chi(\nu, \gamma) = \frac{1}{1+((\nu-\nu_c)/\gamma)^2} = \frac{1}{1+(\bar{\nu}-\bar{\nu}_c)^2}, \quad \text{(Equation 2)}$$

where $\nu_c$ is the line center frequency and $\bar{\nu}=\nu/\gamma$ and $\bar{\nu}_c=\nu_c/\gamma$ are the halfwidth-(HWHM-)normalized frequency and line center frequency, respectively.

As $\exp x \approx (1+x)$ for small x and the gas sample 8 is only weakly absorbing, Equation 1 can be written as:

$$I = T_{Meas}I_L - \quad \text{(Equation 3)}$$
$$T_{Meas}I_L A_{Meas}(T) c_{Meas} p_{Meas} \frac{1}{\pi\gamma_{Meas}} \chi(\nu, \gamma_{Meas}) L_{Meas}.$$

The light 1 of the diode laser 2 is modulated through its injection current i, which imposes modulation on the optical frequency $\nu_L$ and to some extend on the intensity $I_L$ of the emitted light 1. The modulation is performed by a first modulation means 9 generating a sinusoidal signal at a frequency $f_m$ and a second modulation means 10 generating a periodic slow sweep function, which may be part-wise linear in time or of an arbitrary shape. The signals of said first and second modulation means 9 and 10 are summed in adding means 11 and fed to a modulation input of the diode laser 2. Thus, the injection current i of the diode laser 2 is given by:

$$i = i_0(t) + i_a(t)\cos(2\pi f_m t) \quad \text{(Equation 4)},$$

where $i_0(t)$ includes a bias and a slow current function, for example a slow current ramp, and $i_a(t)$ is the modulation amplitude at the modulation frequency $f_m$.

The modulation of the injection current i of the diode laser 2 results in a modulation of the optical frequency $\nu_L$ of the emitted light 1:

$$\nu_L = \nu_0(t) + \nu_a \cos(2\pi f_m t) \quad \text{(Equation 5)},$$

where $\nu_0(t)$ represents a sweep of the optical frequency over the absorption line of interest and $\nu_a$ is the modulation amplitude of the optical frequency $\nu_L$ at the modulation frequency $f_m$. For simplicity it is assumed that the modulation of the optical frequency $\nu_L$ follows the modulation of the injection current i without phase shift.

The modulation of the injection current i of the diode laser 2 also results in modulation of the intensity $I_L$ of the emitted light 1:

$$I_L(\nu_0,\nu_a,t) = I_{L,0}(\nu_0) + \kappa_1\nu_a \cos(2\pi f_m t + \phi) \quad \text{(Equation 6)}$$

where the slow intensity variation due to the sweep of the optical frequency of the light 1 is taken as the DC term $I_{L,0}(\nu_0)$ and $\kappa_1$ is defined as the linear intensity modulation coefficient. The term $\kappa_1\nu_a = I_{L,1}(\nu_0) = m$ represents the intensity modulation amplitude, i.e. the first Fourier component of the intensity modulation, whereas $\phi$ stands for the phase shift between the intensity and frequency modulation. In Equation 5 possible nonlinear terms of the intensity modulation of the emitted light 1 are neglected.

According to the slow sweep function of the second modulation means 10 the optical frequency of the emitted light 1 sweeps over the molecular absorption line of interest of the gas sample 8 in the measurement path 5, while the light 1 is modulated with the frequency $f_m$. Due to the nonlinear wavelength dependent absorption the light 1 will have an overtone spectrum, the harmonic content of the spectrum being dependent on the width and shape of the molecular absorption line.

After passing through the measurement path 5 the light 1 impinges onto a measuring detector 12, the output of which is given by:

$$S_{Meas} = \eta_{Meas}I = \eta_{Meas}T_{Meas}I_L - \quad \text{(Equation 7)}$$
$$\eta_{Meas}T_{Meas}I_L A_{Meas}(T) c_{Meas} p_{Meas} \frac{\chi(\nu, \gamma_{Meas})}{\pi\gamma_{Meas}} L_{Meas},$$

where $\eta_{Meas}$ is an instrument factor of the measurement path 5.

The portion of the light 1 diverted into the monitor path 6 impinges onto a monitor detector 13. Since there is no molecular absorption in the monitor path 6, the monitor detector output is given by:

$$S_{Mon} = \eta_{Mon}I = \eta_{Mon}T_{Mon}I_L = G_{Mon}I_L \quad \text{(Equation 8)},$$

where $\eta_{Mon}$ and $T_{mon}$ are the instrument factor and the transmission factor of the monitor path 6, respectively, and $G_{Mon} = \eta_{Mon}T_{Mon}$ is a constant gain. The monitor detector output $S_{Mon}$ is fed via an analog-to-digital converter 14 and a low-pass filter 15 to a calculating means 16 of the spectroscopy system. The monitor detector output $S_{Mon}$ is further used for correcting any transmission changes in the measurement path 5 and is therefore fed to an automatic gain control unit 17 together with the measuring detector output $S_{Meas}$. In the automatic gain control unit 17 the measuring detector output $S_{Meas}$ is controlled so as to maintain the condition:

$$\eta_{Meas}T_{Meas} = \eta_{Mon}T_{Mon}G_{Mon} \quad \text{(Equation 9)}.$$

Both the intensity I of the light 1 impinging on the measuring detector 12 and the line-shape function $\chi$ are periodic functions of time, so that they can be expressed in terms of a Fourier series:

$$I(\nu_0, \nu_a, t) = \quad \text{(Equation 10)}$$
$$\sum_{n=0}^{\infty} I_n^e(\nu_0, \nu_a)\cos(2\pi n f_m t) + \sum_{n=0}^{\infty} I_n^o(\nu_0, \nu_a)\sin(2\pi n f_m t),$$

$$\chi(\bar{\nu}_0, \bar{\nu}_a, t) = \sum_{n=0}^{\infty} \chi_n^e(\bar{\nu}_0, \bar{\nu}_a, t)\cos(2\pi n f_m t), \quad \text{(Equation 11)}$$

where $\bar{\nu}_0 = \nu_0/\gamma$ and $\bar{\nu}_a = \nu_a/\gamma$ represent the halfwidth-(HWHM-) normalized sweep and the modulation amplitude of the optical frequency $\nu_L$, respectively. As the line-shape function $\chi(\nu_L,t)$ follows the modulation of the frequency without phase delay, only the cosine terms in the series expansion are needed. By inserting Equations 6 and 11 into Equation 7 one obtains an optical-frequency-dependent expression for measuring detector output $S(\nu)_{Meas}$. The gained measuring detector output $S(\nu)_{Meas}$ containing AC components at the modulation frequency $f_m$ and its higher harmonics $2f_m$, $3f_m$, $4f_m$, etc. is demodulated at a higher harmonic $Nf_m$, most commonly at $2f_m$, in a first demodulation means 18 comprising an analog-to-digital converter 19 and a lock-in amplifier 20 for digitizing the gained measuring detector output $S(v)_{Meas}$ and converting it to base band. The illustrated lock-in amplifier 20 includes a reference input 100 such as $Nf_m$. The demodulation at $Nf_m$ shifts the measurement from frequencies near DC, where the light source 2 is noisy, into a higher frequency range, where the noise is lower, thus improving the measurement sensitivity by approximately an order of $10^2$–$10^3$ compared to a direct unmodulated absorption measurement. The in-phase component of the measuring detector output $S(v)_{Meas}$ demodulated at $Nf_m$ can be written as:

$$S(v)^e_{N,Meas} \approx -G_{Mon} A_{Meas}(T) c_{Meas} p_{Meas} \frac{1}{\pi \gamma_{Meas}} \quad \text{(Equation 12)}$$

$$L_{Meas} \left( \begin{array}{c} I^e_{L,0}(v_0) \chi^e_N(\bar{v}_0, \bar{v}_a) + \\ \frac{\kappa_1 v_a \cos\varphi}{2}(\chi^e_{N-1}(\bar{v}_0, \bar{v}_a) + \chi^e_{N+1}(\bar{v}_0, \bar{v}_a)) \end{array} \right).$$

As the phase difference $\varphi$ between the intensity modulation and the frequency modulation of the light 1 at the modulation frequency $f_m$ is close to $\pi$ and consequently $\cos\varphi \approx -1$, $S(v)_{Meas}$ can be rewritten as:

$$S(v)^e_{N,Meas} = c_{Meas} \cdot \underbrace{(G_{Mon} A_{Meas}(T) p_{Meas} L_{Meas})}_{par(T,p)} \cdot \quad \text{(Equation 13)}$$

$$\underbrace{\frac{1}{\pi \gamma_{Meas}} \left( \begin{array}{c} I^e_{L,0}(v_0) \chi^e_N(\bar{v}_0, \bar{v}_a) - \\ \frac{m}{2}(\chi^e_{N-1}(\bar{v}_0, \bar{v}_a) + \chi^e_{N+1}(\bar{v}_0, \bar{v}_a)) \end{array} \right)}_{\Gamma_{Meas}(\bar{v}_0, \bar{v}_a, m, \gamma_{Meas})},$$

where $m = \kappa_1 v_a$ is the intensity modulation amplitude. As shown in Equation 13 the demodulated measuring detector output $S(v)_{Meas}$ can be presented as a product of the concentration. (mole fraction) $c_{Meas}$ of the absorbing gas component, a known pressure and temperature dependent parameter $par(T,p)$ and a function $\Gamma_{Meas}(\bar{v}_0, \bar{v}_a, m, \gamma_{Meas})$ dependent on laser modulation parameters and the width of the molecular absorption line of interest. According to Journal of Quantitative Spectroscopy & Radiative Transfer, 68 (2001) 299-317, which is incorporated herein by reference, the Nth Fourier component of a wavelength modulated Lorentzian line-shape function $\chi_N$ can be expressed by:

$$\chi_N(\bar{v}_0, \bar{v}_a) = \frac{A_N}{\bar{v}_a^N} \left[ B_N + \frac{C_N S_+ + D_N S_-}{\sqrt{2} R} \right]. \quad \text{(Equation 14)}$$

For $N=2$, the Nth, (N−1)th and (N+1)th Fourier components of the line-shape function $\chi$ are needed and the factors of Equation 15 are as follows:

$A_1 = 2-\delta_{1,0}$, $A_2 = 2-\delta_{2,0}$, $A_3 = 2-\delta_{3,0}$, where $\delta_{n,0}$ is the Kronecker delta, $B_1 = 0$, $B_2 = 2$, $B_3 = -8\bar{v}_0$, $C_1 = -\bar{v}_0$, $C_2 = [(2+\bar{v}_a^2)-2\bar{v}_0^2]$, $C_3 = \bar{v}_0[3(4+\bar{v}_a^2)-4\bar{v}_0^2]$, $D_1 = \text{sign}^2(\bar{v}_0)$, $D_2 = -\text{sign}^2(\bar{v}_0)4\bar{v}_0$, $D_3 = -\text{sign}^2(\bar{v}_0)[(4+3\bar{v}_a^2)-12\bar{v}_0^2]$, $R = \sqrt{M^2 + 4\bar{v}_0^2}$, $S_+ = \sqrt{R+M}$ and $S_- = \sqrt{R-M}$, where $M = 1 + \bar{v}_a^2 - \bar{v}_0^2$.

As mentioned above, yet another portion of the light 1 of the diode laser 2 is passed through the reference path 7, which contains in a reference cell of known length $L_{Ref}$ a reference gas 21 comprising the gas component to be detected in the gas sample 8 in a known concentration. After passing through the reference path 7 the light 1 impinges onto a reference detector 22. The reference detector output $S(v)_{Ref}$ is demodulated at the higher harmonic $Nf_m$ in a second demodulation means 23 comprising an analog-to-digital converter 24 and a lock-in amplifier 25. The illustrated lock-in amplifier 25 includes a reference input 110 such as $Nf_m$. As the reference detector output $S(v)_{Ref}$ is processed in the same way as the measuring detector output $S(v)_{Meas}$, the in-phase component of the reference detector output $S(v)_{Ref}$ demodulated at $Nf_m$ can be written by using Equation 13 as:

$$S(v)^e_{N,Ref} = \underbrace{n_{Ref} T_{Ref} A_{Ref}(T) c_{Ref} p_{Ref} L_{Ref}}_{constant} \frac{1}{\pi \gamma_{Ref}} \cdot \quad \text{(Equation 15)}$$

$$\underbrace{\left( \begin{array}{c} I^e_{L,0}(v_0) \chi^e_N(\bar{v}_0, \bar{v}_a) - \\ \frac{m}{2}(\chi^e_{N-1}(\bar{v}_0, \bar{v}_a) + \chi^e_{N+1}(\bar{v}_0, \bar{v}_a)) \end{array} \right)}_{\Gamma_{Ref}(\bar{v}_0, \bar{v}_a, m)}.$$

Since the product $\eta_{Ref} T_{Ref} A_{Ref}(T) c_{Ref} p_{Ref} L_{Ref}$ is constant, the demodulated reference detector output $S(v)_{N,Ref}$ can be written as a product of a constant value and a function $\Gamma_{Ref}(\bar{v}_0, \bar{v}_a, m)$, which is solely dependent on laser modulation parameters, since the half width $\gamma_{Ref}$ of the reference absorption line is also constant.

The demodulated measuring detector output $S(v)_{N,Meas}$ and reference detector output $S(v)_{N,Ref}$ and the low-pass filtered monitor detector output $S_{Mon,LP}$ are fed to the calculating means 16 for calculating the concentration of the gas component in the gas sample 8 and for automatically correcting any changes of the FM/AM parameters of the diode laser 2 in real time.

FIG. 2 shows a functional block diagram of the calculating means 16. In block 26 the average value $I_{L,0}(v)$ of the intensity of the modulated light 1 is calculated from the low-pass filtered monitor detector output $S_{Mon,LP}$ and the known constant gain $G_{Mon}$ by using Equation 8. In block 27 Equation 15 is applied to the demodulated reference detector output $S(v)_{N,Ref}$. Since $I_{L,0}(v)$ is provided and the width $\gamma_{Ref}$ of the reference absorption line is constant, the laser modulation parameters, i. e. the intensity modulation amplitude m and the frequency modulation amplitude $v_a$ can be extracted. It should be noted that the gas in the reference path 7 does not have to be the same as the gas component to be measured in the measurement path 5. What is crucial is that the concentration, temperature and pressure of the gas in the reference path 7 are kept constant, thus assuring a constant width $\gamma_{Ref}$ of the reference absorption line. The parameters $v_a$ and m are then used for determining the concentration $c_{Meas}$ of the gas component of interest in the measurement path 5 by fitting Equation 13 to the demodulated measuring detector output $S(v)_{N,Meas}$ in block 28 and dividing the result $c_{Meas} par(T,p)$ by the known parameter $par(T,p)$ in block 29.

This method allows real time monitoring of any changes in FM/AM laser characteristics in the frequency band around $f_m$ and any drifts of the sine amplitude generated in the first modulation means 9.

For correcting any FM changes in the slow sweep function from the second modulation means 10 the width $\gamma_{Ref}$ of the reference absorption line is extracted from the fit of Equation 15 to the demodulated reference detector output $S(\gamma)_{N,Ref}$ in block 27 and afterwards compared to an initial recorded value $\gamma_{Ref,initial}$ in block 30. The ratio is then fed to a sweep control unit 31, which controls the amplitude of the slow sweep function generated by the second modulation means 10.

The invention claimed is:

1. A wavelength modulation spectroscopy method for measuring the concentration ($c_{Meas}$) of a gas component of interest in a gas sample, the method comprising the steps of:

passing a portion of the light of a light source through a reference gas and thereafter to a reference detector, the reference gas comprising the gas component of interest or another suitable gas component in a known concentration;

passing another portion of the light through the gas sample and thereafter to a measuring detector;

modulating the wavelength of said light with a frequency ($f_m$), while the wavelength is swept over an absorption line of the gas component;

demodulating the reference detector output ($S(\nu)_{Ref}$) at a higher harmonic ($Nf_m$) of said frequency ($f_m$);

providing a mathematical description of the demodulated reference detector output ($S(\nu)_{N,Ref}$) based on Fourier analysis of the modulated light and on a mathematical expression for the absorption line, said mathematical description comprising unknown modulation parameters with respect to the modulation of the light;

determining said modulation parameters from the demodulated reference detector output ($S(\nu)_{N,Ref}$) and its mathematical description; and generating an output signal representative of the measurement.

2. The method according to claim 1, wherein the Lorentzian line-shape function is used for the mathematical expression for the absorption line.

3. The method according to claim 1, further comprising the steps of:

directing another portion of the light to a monitor detector, and wherein the mathematical description of the demodulated reference detector output ($S(\nu)_{N,Ref}$) contains an average value of the intensity of the modulated light, and wherein said average value is extracted from the monitor detector output ($S(\nu)_{Mon}$) by low-pass filtering.

4. The method according to claim 2, further comprising the steps of:

directing another portion of the light to a monitor detector, and wherein the mathematical description of the demodulated reference detector output ($S(\nu)_{N,Ref}$) contains an average value of the intensity of the modulated light, and wherein said average value is extracted from the monitor detector output ($S(\nu)_{Mon}$) by low-pass filtering.

5. The method according to claim 1, wherein the mathematical description of the demodulated reference detector output ($S(\nu)_{N,Ref}$) is given by:

$$S(\nu)^e_{N,Ref} = \eta_{Ref} T_{Ref} A_{Ref}(T) c_{Ref} p_{Ref} L_{Ref} \frac{1}{\pi \gamma_{Ref}} \left( \begin{array}{c} I^e_{L,0}(\nu_0) \chi^e_N(\overline{\nu}_0, \overline{\nu}_a) - \\ \frac{m}{2}(\chi^e_{N-1}(\overline{\nu}_0, \overline{\nu}_a) + \chi^e_{N+1}(\overline{\nu}_0, \overline{\nu}_a)) \end{array} \right),$$

where $\eta_{Ref}$ is an instrument factor and $T_{Ref}$ a transmission factor over a reference path containing the reference gas and having a length $L_{Ref}$, $A_{Ref}(T)$ and $\chi^e_N(\overline{\nu}_0, \overline{\nu}_a)$ represent the intensity and the N-th Fourier component of the peak-normalized shape of a molecular absorption line of interest in the reference gas, respectively, $\gamma_{Ref}$ is the half width at half maximum (HWHM) of the absorption line, $c_{Ref}$ is the mole fraction of the absorbing gas component, $p_{Ref}$ is the total pressure in the reference path, $I^e_{L,0}(\nu_0)$ is the intensity of the light in a DC band, and $m$ and $\nu_a$ represent an intensity and a frequency modulation parameter, respectively.

6. The method according to claim 2, wherein the mathematical description of the demodulated reference detector output ($S(\nu)_{N,Ref}$) is given by:

$$S(\nu)^e_{N,Ref} = \eta_{Ref} T_{Ref} A_{Ref}(T) c_{Ref} p_{Ref} L_{Ref} \frac{1}{\pi \gamma_{Ref}} \left( \begin{array}{c} I^e_{L,0}(\nu_0) \chi^e_N(\overline{\nu}_0, \overline{\nu}_a) - \\ \frac{m}{2}(\chi^e_{N-1}(\overline{\nu}_0, \overline{\nu}_a) + \chi^e_{N+1}(\overline{\nu}_0, \overline{\nu}_a)) \end{array} \right),$$

where $\eta_{Ref}$ is an instrument factor and $T_{Ref}$ a transmission factor over a reference path containing the reference gas and having a length $L_{Ref}$, $A_{Ref}(T)$ and $\chi^e_N(\overline{\nu}_0, \overline{\nu}_a)$ represent the intensity and the N-th Fourier component of the peak-normalized shape of a molecular absorption line of interest in the reference gas, respectively, $\gamma_{Ref}$ is the half width at half maximum (HWHM) of the absorption line, $c_{Ref}$ is the mole fraction of the absorbing gas component, $p_{Ref}$ is the total pressure in the reference path, $I^e_{L,0}(\nu_0)$ is the intensity of the light in a DC band, and $m$ and $\nu_a$ represent an intensity and a frequency modulation parameter, respectively.

7. The method according to claim 3, wherein the mathematical description of the demodulated reference detector output ($S(\nu)_{N,Ref}$) is given by:

$$S(\nu)^e_{N,Ref} = \eta_{Ref} T_{Ref} A_{Ref}(T) c_{Ref} p_{Ref} L_{Ref} \frac{1}{\pi \gamma_{Ref}} \left( \begin{array}{c} I^e_{L,0}(\nu_0) \chi^e_N(\overline{\nu}_0, \overline{\nu}_a) - \\ \frac{m}{2}(\chi^e_{N-1}(\overline{\nu}_0, \overline{\nu}_a) + \chi^e_{N+1}(\overline{\nu}_0, \overline{\nu}_a)) \end{array} \right),$$

where $\eta_{Ref}$ is an instrument factor and $T_{Ref}$ a transmission factor over a reference path containing the reference gas and having a length $L_{Ref}$, $A_{Ref}(T)$ and $\chi^e_N(\overline{\nu}_0, \overline{\nu}_a)$ represent the intensity and the N-th Fourier component of the peak-normalized shape of a molecular absorption line of interest in the reference gas, respectively, $\gamma_{Ref}$ is the half width at half maximum (HWHM) of the absorption line, $c_{Ref}$ is the mole fraction of the absorbing gas component, $p_{Ref}$ is the total pressure in the reference path, $I_{L,0}{}^e(v_0)$ is the intensity of the light in a DC band, and m and $v_a$ represent an intensity and a frequency modulation parameter, respectively.

8. The method according to claim 4, wherein the mathematical description of the demodulated reference detector output $(S(v)_{N,Ref})$ is given by:

$$S(v)^e_{N,Ref} = \eta_{Ref} T_{Ref} A_{Ref}(T) c_{Ref} p_{Ref} L_{Ref} \frac{1}{\pi \gamma_{Ref}} \left( \frac{I^e_{L,0}(v_0) \chi^e_N(\overline{v}_0, \overline{v}_a) - }{\frac{m}{2}(\chi^e_{N-1}(\overline{v}_0, \overline{v}_a) + \chi^e_{N+1}(\overline{v}_0, \overline{v}_a))} \right),$$

where $\eta_{Ref}$ is an instrument factor and $T_{Ref}$ a transmission factor over a reference path containing the reference gas and having a length $L_{Ref}$, $A_{Ref}(T)$ and $\chi_N{}^e(\overline{v}_0, \overline{v}_a)$ represent the intensity and the N-th Fourier component of the peak-normalized shape of a molecular absorption line of interest in the reference gas, respectively, $\gamma_{Ref}$ is the half width at half maximum (HWHM) of the absorption line, $c_{Ref}$ is the mole fraction of the absorbing gas component, $p_{Ref}$ is the total pressure in the reference path, $I_{L,0}{}^e(v_0)$ is the intensity of the light in a DC band, and m and $v_a$ represent an intensity and a frequency modulation parameter, respectively.

9. The method according to claim 1, further comprising the steps of:

demodulating the measuring detector output $(S(v)_{Meas})$ at said higher harmonic $(Nf_m)$ of said frequency $(f_m)$;

providing a further mathematical description of the demodulated measuring detector output $(S(v)_{N,Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(c_{Meas})$ of the gas component from the demodulated measuring detector output $(S(v)_{N,Meas})$, its mathematical description and the determined modulation parameters.

10. The method according to claim 2, further comprising the steps of:

demodulating the measuring detector output $(S(v)_{Meas})$ at said higher harmonic $(Nf_m)$ of said frequency $(f_m)$;

providing a further mathematical description of the demodulated measuring detector output $(S(v)_{N,Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(c_{Meas})$ of the gas component from the demodulated measuring detector output $(S(v)_{N,Meas})$, its mathematical description and the determined modulation parameters.

11. The method according to claim 3, further comprising the steps of:

demodulating the measuring detector output $(S(v)_{Meas})$ at said higher harmonic $(Nf_m)$ of said frequency $(f_m)$;

providing a further mathematical description of the demodulated measuring detector output $(S(v)_{N,Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(c_{Meas})$ of the gas component from the demodulated measuring detector output $(S(v)_{N,Meas})$, its mathematical description and the determined modulation parameters.

12. The method according to claim 4, further comprising the steps of:

demodulating the measuring detector output $(S(v)_{Meas})$ at said higher harmonic $(Nf_m)$ of said frequency $(f_m)$;

providing a further mathematical description of the demodulated measuring detector output $(S(v)_{N,Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(c_{Meas})$ of the gas component from the demodulated measuring detector output $(S(v)_{N,Meas})$, its mathematical description and the determined modulation parameters.

13. The method according to claim 5, further comprising the steps of:

demodulating the measuring detector output $(S(v)_{Meas})$ at said higher harmonic $(Nf_m)$ of said frequency $(f_m)$;

providing a further mathematical description of the demodulated measuring detector output $(S(v)_{N,Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(C_{Meas})$ of the gas component from the demodulated measuring detector output $(S(v)_{N,Meas})$, its mathematical description and the determined modulation parameters.

14. The method according to claim 6, further comprising the steps of:

demodulating the measuring detector output $(S(v)_{Meas})$ at said higher harmonic $(Nf_m)$ of said frequency $(f_m)$ providing a further mathematical description of the demodulated measuring detector output $(S(v)_{Meas})$ based on Fourier analysis of the modulated light and on a mathematical expression for the absorption line, said further mathematical description comprising said unknown modulation parameters and the unknown concentration $(c_{Meas})$ of the gas component of interest in the gas sample; and determining said concentration $(c_{Meas})$ of the gas component from the demodulated measuring detector output $(S(v)_{N,Meas})$, its mathematical description and the determined modulation parameters.

15. The method according to claim 7, further comprising the steps of:

demodulating the measuring detector output $(S(v)_{Meas})$ at said higher harmonic $(Nf_m)$ of said frequency $(f_m)$ providing a further mathematical description of the demodulated measuring detector output ($S(v)_{N,Meas}$) based on Fourier analysis of the modulated light and on a mathematical expression for the absorption line, said further mathematical description comprising said unknown modulation parameters and the unknown concentration ($c_{Meas}$) of the gas component of interest in the gas sample; and determining said concentration ($c_{Meas}$) of the gas component from the demodulated measuring detector output ($S(v)_{N,Meas}$), its mathematical description and the determined modulation parameters.

16. The method according to claim 8, further comprising the steps of:

demodulating the measuring detector output ($S(v)_{Meas}$) at said higher harmonic ($Nf_m$) of said frequency ($f_m$)

providing a further mathematical description of the demodulated measuring detector output ($S(v)_{N,Meas}$) based on Fourier analysis of the modulated light and on a mathematical expression for the absorption line, said further mathematical description comprising said unknown modulation parameters and the unknown concentration ($c_{Meas}$) of the gas component of interest in the gas sample; and determining said concentration ($c_{Meas}$) of the gas component from the demodulated measuring detector output ($S(v)_{N,Meas}$), its mathematical description and the determined modulation parameters.

17. The method according to claim 9, wherein the mathematical description of the demodulated measuring detector output ($S(v)_{N,Meas}$) is given by:

$$S(v)_{N,Meas}^e = c_{Meas} par(T, p) \frac{1}{\pi \gamma_{Meas}} \left( \begin{array}{c} I_{L,0}^e(v_0) \chi_N^e(\overline{v}_0, \overline{v}_a) - \\ \frac{m}{2} (\chi_{N-1}^e(\overline{v}_0, \overline{v}_a) + \chi_{N+1}^e(\overline{v}_0, \overline{v}_a)) \end{array} \right),$$

where $c_{Meas}$ is the concentration (mole fraction) of the gas component to be measured, par(T,p) is a known parameter dependent on the pressure and temperature in the gas sample, having a length $L_{Meas}$, $\alpha_0$ and $\chi_N(v)$ represent the peak absorbance and the Nth Fourier component of the peak-normalized shape of said molecular absorption line, respectively, $I_{L,0}$ is the average value of the intensity of the modulated light and m is the modulation parameter, $\chi_N^e(\overline{v}_0, \overline{v}_a)$ represent the N-th Fourier component of the peak-normalized shape of a molecular absorption line of interest in the gas sample, $\gamma_{Meas}$ is the half width at half maximum (HWHM) of the absorption line, $I_{L,0}^e(v_0)$ is the intensity of the light in a DC band, and m and $v_a$ represent an intensity and a frequency modulation parameter, respectively.

* * * * *